United States Patent [19]

Blumenstein et al.

[11] Patent Number: 5,190,969
[45] Date of Patent: Mar. 2, 1993

[54] 2,3-EPOXY DERIVATIVES AS ANTI RETROVITAL CHEMOTHERAPEUTIC AGENTS

[75] Inventors: Jeffrey J. Blumenstein, Germantown; Christopher J. Michejda; Stephen Oroszlan, both of Potomac; Terry Copeland, Frederick, all of Md.

[73] Assignee: The United States of America as represented by the Secretary of the Department of Health & Human Services, Washington, D.C.

[21] Appl. No.: 286,977

[22] Filed: Dec. 20, 1988

[51] Int. Cl.$^5$ .................. A61K 31/40; A61K 31/335
[52] U.S. Cl. .................. 514/422; 548/517; 549/548; 514/475
[58] Field of Search ............. 548/336, 465, 496, 517; 549/548, 549, 555; 514/397, 414, 422, 475

[56] References Cited

U.S. PATENT DOCUMENTS 2,996,521 8/1961 Matthews et al. ............... 260/349

OTHER PUBLICATIONS

Ikuta et al, Virology, 154, pp. 207-213 (1986).
Ikuta et al, Virology, 154, pp. 195-206 (1986).
Katoh et al, Virus Research, 5, pp. 265-276 (1986).
Gao et al, J. Am. Chem. Soc., 109, pp. 5765-5780 (1987).
Omura et al, Antimicrobial Agents and Chemotherapy, vol. 6, No. 2, pp. 207-215 (1974).
Goldfine et al, Biochimica et Biophysica Acta, 512, pp. 229-240 (1978).

Primary Examiner—Mary C. Lee
Assistant Examiner—Mary Susan H. Gabilan
Attorney, Agent, or Firm—Birch, Stewart, Kolasch & Birch

[57] ABSTRACT

The present invention is related to compounds, compositions and methods of treating viral infections. Compounds of the present invention have the following general formula:

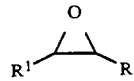

wherein R is selected from $-CH_2OH$, $-CO_2R^2$, $-CONR^3R^4$, or $COR^5$, wherein $R^2$ is hydrogen or a lower alkyl group, $R^3$ and $R^4$ are each independently hydrogen or a lower alkyl group, $R^5$ is an amino acid residue bound via a terminal nitrogen or peptide having at least two amino acid residues; and wherein $R^1$ is $C_5$-$C_{13}$ alkyl, aryl, aralkyl, aralkyl(lower alkyl) ether, or $C_5$-$C_{13}$ alkyl (lower alkyl)ether.

9 Claims, No Drawings

2,3-EPOXY DERIVATIVES AS ANTI RETROVITAL CHEMOTHERAPEUTIC AGENTS

BACKGROUND OF THE INVENTION

Retroviruses have long been associated with neoplastic disease in avian and mammalian species. The discovery of infectious human retroviruses which are associated with malignancies has spawned a surge of interest in these agents. Recent work linking a retrovirus, Human Immunodeficiency Virus (HIV), as an etiologic agent of Acquired Immune Deficiency Syndrome (AIDS) (Gallo, R. C. (1987) *Sci. Amer.*, 256, 47–56) has further intensified this interest.

Research on antiviral agents has progressed far in the past decade in response to the need to treat infections of HIV. The majority of the work on antiretrovirals has focused on the use of nucleoside derivatives as inhibitors of the retroviral reverse transcriptase (Fischl, M. A., et al., *N. Eng. J. Med.*, 317, 185–191 (1987); J. E. Dahlberg, H. Mitsuya, S. B. Blum, S. Broder and S. A. Aaronson, *Proc. Natl. Acad. Sci.*, 84, 2469–2473 (1987); S. Broder, in "*Human Retroviruses, Cancer, and AIDS*", D. Bolognes; ed., Alan R. Liss, Inc., NY, 1988, pp. 365–380; M. S. Hirsh and J. C. Kaplan, *Antimic Agents and Chemotherapy*, 31, 839–843 (1987). Many of these agents have characteristics which restrict their clinical utility (D. D. Richman, et al., *N. Eng. J. Med.*, 317, 192–197 (1987); Terasaki, T., Pardridge, W. M., *J. Infect. Disease*, 158, 630–632 (1988)).

Viral proteases are one of the enzymes which are essential components of virion assembly (J. Wellink and A. Van Kammen, *Arch. Virol.*, 98, 1–26 (1988)). Site specific mutagenesis of the presumed active site of retroviral proteases has demonstrated that active enzyme is necessary for the production of mature, infectious virus particles (I. Katoh, et al, *Virology*, 145, 280–292 (1985); N. E. Kohl, et al. *Proc. Natl. Acad. Sci.*, 85, 4686–4690 (1988); S. Seelmeier, H. Schmidt, V. Tura, and K. von der Helm, *Proc. Natl. Acad. Sci.*, 85, 6612–6616 (1988)). Consequently, interference of proteolytic processing through the use of enzyme inhibitors is an attractive chemotherapeutic target for the treatment of viral diseases. Expression of HIV protease in *E. coli* (S. Seelmeier, H. Schmidt, V. Tura, and K. von der Helm, *Proc. Natl. Acad. Sci.*, 85, 6612–6616 (1988); M. C. Graves, J. J. Lim, E. P. Heimer and R. A. Kramer, *Proc. Natl. Acad. Sci.*, 85, 2449–2453 (1988); C. De-Bouck, et al., *Proc. Natl. Acad. Sci.*, 84, 8903–8906 (1987); J. Mous, E. P. Heimer and S. F. J. Le Grice, *J. Virol.*, 62, 1433–1436 (1988)), and chemical synthesis (T. D. Copeland and S. Oroszlan, *Gene Anal. Tech.*, 5, 109–115 (1988); J. Schneider and S. B. H. Kent, Cell, 54, 363–368 (1988); R. F. Nutt, et al, *Proc. Natl. Acad. Sci.*, 85, 7129–7133 (1988)) of active enzyme have provided in vitro systems to facilitate the study of this protein.

The antifungal antibiotic cerulenin, 4-Oxo-2R,3S-epoxy-trans,trans-2,5-dodecadienyl amide has been reported to exhibit antiretroviral activity against Rous Sarcoma Virus (H. Goldfine, J. B. Harley and J. A. Wyke, *Biochem. Biophys. Acad.*, 512, 229–240 (1978)) and Murine Leukemia Virus (I. Katoh, Y. Yoshinaka and R. B. Luftig, *Virus Res.*, 5, 265–276 (1986)) in vitro. Originally studied for its inhibition of fatty acid synthesis through the inhibition of β-ketoacetyl transferase, (for review, see S. Omura, *Bacteriological Rev.*, 40, 681–697 (1976)) cerulenin apparently interferes with polypeptide processing during virus particle assembly (K. Ikuta and R. B. Luftig, *Virology*, 154, 195–206 (1986)). It has been uncertain at what stage of processing the inhibition was occurring, but interference with enzyme catalyzed proteolytic cleavage of virus precursor polypeptides has been assumed to be likely. Cerulenin has also been recently reported to inhibit viral polyprotein processing in HIV infected cells (Pal, R., et al (1988), *Proc. Natl. Acad. Sci.*, 85, 9283–9286). Since cerulenin is a potent inhibitor of fatty acid synthesis, it exhibits a relatively high toxicity (Matsumae, *J. Antibiotic.*, 17a, 1 (1964); Pal, R. et al (1988)). The present invention has been discovered with the above background and disadvantages in mind.

SUMMARY OF THE INVENTION

The present invention is related to compounds useful in treating viral infections. The compounds of the present invention have the following general formula:

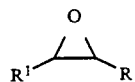

wherein R is selected from —CH$_2$OH, —CO$_2$R$^2$, —CONR$^3$R$^4$ or COR$^5$, wherein R$^2$ is hydrogen or a lower alkyl group, R$^3$ and R$^4$ are each independently hydrogen or a lower alkyl group, R$^5$ is an amino acid residue bound via a terminal nitrogen on said amino acid or a peptide having at least two amino acid residues; and wherein R$^1$ is aralkyl, aralkyl(lower alkyl)ether or C$_5$-C$_{13}$ alkyl(lower alkyl)ether.

The compound of the present invention also includes compounds having the general formula:

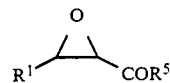

wherein R$^5$ is an amino acid residue bound via a terminal nitrogen on said amino acid or a peptide having at least two amino acid residues; and wherein R$^1$ is C$_5$-C$_{13}$ alkyl.

The present invention is also directed to compositions comprising a compound having the formula:

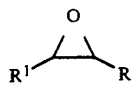

wherein R is selected from —CH$_2$OH, —CO$_2$R$^2$, —CONR$^3$R$^4$, or COR$^5$, wherein R$^2$ is hydrogen or a lower alkyl group, R$^3$ and R$^4$ are each independently hydrogen or a lower alkyl group, R$^5$ is an amino acid residue bound via a terminal nitrogen on said amino acid, or a peptide having at least two amino acid residues; and wherein R$^1$ is aralkyl, aralkyl(lower alkyl)ether or C$_5$-C$_{13}$ alkyl(lower alkyl)ether; and a pharmaceutically acceptable carrier, as well as compositions comprising a compound having the formula:

wherein $R^5$ is an amino acid residue bound via a terminal nitrogen on said amino acid, or a peptide having at least two amino acid residues; and wherein $R^1$ is $C_5$–$C_{13}$ alkyl, and a pharmaceutically acceptable carrier.

Further, the present invention is directed to a method of treating viral infections to a host in need thereof by administering an anti-viral effective amount of the compound having the formula:

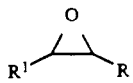

wherein R is selected from —$CH_2OH$, —$CO_2R^2$, —$CONR^3R^4$, or $COR^5$, wherein $R^2$ is hydrogen or a lower alkyl group, $R^3$ and $R^4$ are each independently hydrogen or a lower alkyl group, $R^5$ is an amino acid residue bound via a terminal nitrogen or peptide having at least two amino acid residues; and wherein $R^1$ is $C_5$–$C_{13}$ alkyl, aryl, aralkyl, aralkyl(lower alkyl)ether, or $C_5$–$C_{13}$ alkyl(lower alkyl)ether. By host is meant members from the classes of mammals or aves, or any animal in need of anti viral therapy.

By lower alkyl is meant $C_1$–$C_4$, straight, and branched hydrocarbon chains.

By aryl is meant an organic radical derived from an aromatic hydrocarbon by removal of one atom. An example of an aryl is a phenyl group.

By arakyl is meant an arylated alkyl wherein an alkyl H atom is substituted by an aryl group. The alkyl group can be a straight of branched chain having 1–6 carbon atoms.

By amino acid residue is meant any of the naturally occurring or synthetic amino acids commonly found or synthesized. Examples of the naturally occurring amino acids are glycine, alanine, valine, leucine, isoleucine, methionine, proline, pheylalanine, tryptophan, serine, threonine, cysteine, tyrosine, asparginine, glutamine, aspartic acid, glutamic acid, lysine, arginine, histidine and the like.

By aralkyl is meant an arylated alkyl group having an alkyl chain length of from 5 to 13 carbon atoms.

By aralkyl (lower alkyl) ether is meant a aralkyl group attached via an ether linkage to a lower alkyl chain having from 1 to 4 carbon atoms.

Of the viral infections that can be treated, any virus, which encodes for a protease, could be treated with the compounds of the present invention. Retroviral infections can be treated with the compounds of the present invention. Examples of such viruses are Type C, Type D retroviruses, HTLV-1, HTLV-2, HIV-1, HIV-2, murine leukemia virus, murine mammary tumor virus, feline leukemia virus, bovine leukemia virus, equine infectious anemia virus, avian sarcoma viruses such as rous sarcoma virus, and the like.

These and other advantages achieved by the present invention will become apparent upon reading of the Detailed Description of the Preferred Embodiments.

DETAILED DESCRIPTION OF THE PREFERRED EMBODIMENTS

Generally, the process of the present invention involves the asymmetric epoxidation of the allylic alcohol by the method of Gao et al. (*J. Am. Chem. Soc.*, 1987, 109 5765–80) with (+) -diisopropyl tartrate (DIPT), tert- butylhydroperoxide (TBHP), and titanium tetraisopropoxide in the presence of 4A powdered molecular sieves to produce the 2S-epoxy alcohol. The allylic-alcohol is obtained by 1) metallation of the acetylene followed by reaction with formaldehyde to afford a propargyl alcohol which is selectively hydrogenated with Lindlars catalyst or 2) metallation of the acetylene followed by reaction with formaldehyde to afford a propargyl alcohol which is partially reduced with sodium bis(2-methoxyethoxy) aluminum hydride or 3) monoalkylation of cis-2-butene-1,4-diol. The epoxy alcohol may be oxidized by 1) $RuCl_3$/ $H_5IO_6$ or 2) pyridinium dichromate in DMF, to yield the epoxy acid. Esterification of the acid with $CH_2N_2$ followed by treatment with $NH_4OH$/MeOH affords the epoxy amide. Alternatively, the acid may be used to acylare a variety of nucleophilic substrates via its mixed anhydride by reaction of the epoxy acid with iso-butyl chloroformate and triethylamine in THF followed by nucleophile ($NH_4OH$, $RNH_2$, $R^2NH$, erc). Epoxidation with (−)-diisopropyl tartrate rather than (+)-diisopropyl tartrate in the above reaction scheme will afford the opposite optical isomer.

The following examples, which are directed to the process of preparing specific compounds, is in no way to be construed as limiting the inventive scope of the present invention. All percentages are by weight unless expressly stated to the contrary. Where necessary, the source of the starting materials are identified.

Experimental

All solvents were reagent grade and were used as received unless noted otherwise. Tetrahydrofuran was freshly distilled from benzophenone ketyl prior to use. Dichloromethane was dried over 3A molecular sieves overnight. $Ti(OiPr)_4$ and tartrate esters were obtained from Aldrich Chem., distilled under reduced pressure and stored under argon prior to use. Triethylamine was distilled from $CaC_2$. Acetylenic substrates, 2-decyn-1-ol, and cis-2-decene were obtained from either Farchan Labs or Wiley Chem. and were used as received. Aqueous tert-butylhydroperoxide was obtained from Aldrich and the isooctane solution prepared as described by Gao et al. (*J. Am. Chem. Soc.,* 1987, 109, 5765–80). All other reagents were obtained from Aldrich Chemicals and were used as received. Flash chromatography was performed as described by Still et al. (*J. Org. Chem.* 1978, 43, 2923–25). NMR spectra Were obtained on a Varian XL-200 or a Nicolet NT-300 in $CDCl_3$ and are reported in ppm downfield from TMS. Mass spectra were obtained on a VG-Micromass ZAB-2F mass spectrometer. Melting points and boiling points are uncorrected.

EXAMPLE 1

Preparation of 2-Dodecyn-1-ol

An anhydrous solution of 49.5 g (325 mmole) of 1-undecyne in 600 ml of ether was prepared under argon and cooled to −20° C. A solution of n-BuLi in hexanes (130 ml, 2.5M, 325 mmole) was then added to the acetylene solution dropwise over about 1.5 H. By the end of the addition a heavy white precipitate has formed. The cooling bath was removed and the solution was stirred for an additional hour. Paraformaldehyde (10.76 g, 358 mmole) was then added in one portion and the mixture was allowed to stir at room temperature under argon overnight. Saturated $NH_4Cl$ (400 ml) was then added cautiously to the mixture with vigorous stirring and cooling as necessary. The ether layer was separated and washed twice with 200 ml of water and 200 ml of brine, dried over MgSO₄, filtered, and the solvent evaporated to afford a cloudy oil. Distillation affords 49.62 g of a clear oil, bp 95°-105° C.(0.1 mm), which solidified upon standing. $^1$H NMR δ4.25 (m, 2), 2.21 (tt, 2, J=2, 7 Hz), 1.6-1.1 (m, 14), 0.88 (t, 3, J=7 Hz).

EXAMPLE 2

Preparation of 2-Tetradecyn-1-ol

2-Tetradecyn-1-ol was prepared as described above for 2-dodecyn-1-ol except that 5.0 g (27 mmole) of 1-tridecyne in 200 ml of ether, 11.6 ml (29 mmole) of n-BuLi, and 874 mg (29 mmole) of paraformaldehyde was used. The reaction afforded a white solid after workup which was crystallized from petroleum ether to yield 4.78 g of white crystals, mp 44°-6° C. $^1$H NMR δ4.25 (m, 2), 2.20 (m, 2), 1.6-1.2 (m, 20), 0.88 (t, 3, J=7 Hz).

EXAMPLE 3

Preparation of cis-2-Decen-1-ol

To a solution of 10.0 g of 2-decyn-1-ol in 150 ml petroleum ether was added 500 mg of Pd on CaCO₃ poisoned with lead (Lindlar catalyst). Quinoline (2.0 ml) was then added to this mixture and the flask was evacuated (house vacuum, ca. 50 mm Hg) and flushed with H₂ three times and left under a H₂ atmosphere. The mixture was stirred vigorously until uptake of H₂ was no longer evident and TLC (SiO₂/20% ether:pet. ether) showed no starting material. The catalyst was removed by filtration through a 4 cm pad of celite and the filtrate was washed two times with 100 ml of 1N HCl, once with 100 ml of saturated NaHCO₃, once with 100 ml of brine, dried over MgSO₄, filtered and the solvent evaporated to give a pale yellow oil. Kugelrohr distillation (100°-120° C. oven, 0.2 mm) affords 8.81 g of clear oil. $^1$H NMR δ5.57 (m,2), 4.20 (t, 2, J=5 Hz), 2.07 (dd, 2, J=6, 12 Hz), 1.5-1.1 (m, 10), 0.88 (t, 3, J=7 Hz).

EXAMPLE 4

Preparation of cis-2-Dodecen-1-ol cis-2-Dodecen-1-ol was prepared as described above for cis-2-decen-1-ol except that 35 g of 2-dodecyn-1-ol, 1.0 g of catalyst, and 3.0 ml of quinoline was used. A clear oil, 33.86 g, was obtained after kugelrohr distillation. $^1$H NMR δ5.57 (m, 2), 4.19 (d, 2, J=5 Hz), 2.07 (dd, 2, J=6, 12 Hz), 1.5-1.2 (m, 14), 0.88 (t, 3, J=7 HZ).

EXAMPLE 5

Preparation of cis-2-Tetradecen-1-ol cis-2-Tetradecen-1-ol was prepared as described above for cis-2-decen-1-ol except that 1.0 g of 2-tetradecyn-1-ol, 50 mg of catalyst, and 0.10 ml of quinoline was used. A clear oil, 0.72 g, was obtained after kugelrohr distillation. $^1$H NMR δ5.57 (m, 2) 4.19 9d, 2, J=6 Hz), 2.07 (dd, 2, J=6, 13 Hz), 1.5-1.2 (m, 18), 0.88 (t, 3, J=7 Hz).

EXAMPLE 6

Preparation of 4-Benzyloxy-(cis)-2-buten-1-ol

4-Benzyloxy-(cis)-2-buten-1-ol was prepared by the method of Danishefski et al. (*J. Am. Chem. Soc.* 1985, 107, 3891-8). A clear oil was obtained after kugelrohr distillation. $^1$H NMR δ7.4-7.3 (m, 5), 5.79 (m, 2), 4.53 (s, 2), 4.14 (m, 4), 1.85 (br, 1)

EXAMPLE 7

Preparation of 4-Heptyloxy-(cis)-2-buten-1-ol

A 50% oil dispersion of NaH (9.4 g) was washed three times with 20 ml of dry THF under argon and the remaining oil-free NaH was suspended in 600 ml of dry THF. cis-2-Butene-1,4-diol (50 ml, 46.7 g, 530 mmole) was then added slowly by syringe to the suspension. After a small amount of diol was added a gelatinous precipitate began to form, most of which went back into solution by the end of the addition. The mixture was allowed to stir for an additional hour and n-heptyliodide (30.4 ml, 42.0 g, 186 mmole) was added in one portion. The reaction was allowed to stir overnight. Aqueous NH₄Cl was added to the mixture followed by 600 ml of ether. The organic layer was separated, washed with 200 ml of NaHCO₃, 200 ml of brine, dried over MgSO₄, filtered and the solvent evaporated to yield a pale yellow oil. Distillation afforded 23.82 g, bp 106°-10° C.(0.1 mm). $^1$H NMR δ5.76 (m, 2), 4.20 (t, 2, J=6 Hz), 4.04 (d, 2, J=6 Hz), 3.44 (t, 2, J=7 hz), 2.22 (t, 1, J=6 Hz), 1.59 (br t, 2, J=7 hz) 1.29 (br, 8), 0.88 (t, 3, J=7 hz).

EXAMPLE 8

Preparation of trans-2-Decen-1-ol.

trans-2-Decen-1-ol was prepared by reduction of the propargyl alcohol by the method described by Jones and Denmark (*Org. Syn.*, 1985, 64, 182-8) using 15 g (97 mmole) of 2-decyn-1-ol in 40 ml of ether and 48 ml (162 mmole) of Red-Al (sodium bis(2-methoxyethoxy)aluminum hybride) in 50 ml of ether. Kugelrohr distillation afforded 11.59 g of a clear oil. $^1$H NMR δ5.66 (m, 2), 4.07 (d, 2, J=5 Hz), 20.3 (dd, 2, J=6, 13 hz), 1.68 (br, 1), 1.4-1.2 (m, 10), 0.88 (t, 3, J=7 Hz).

EXAMPLE 9

Preparation of trans-2-Dodecen-1-ol trans-2-Dodecen-1-ol was prepared by reduction of the propargyl alcohol by the method described by Jones and Denmark (*Org. Syn.*, 1985, 64, 182-8) using 6.0 g (33 mmole) of 2-dodecyn-1-ol in 25 ml of ether and 16.2 ml of Red-Al in 30 ml of ether. Kugelrohr distillation afforded 5.73 g of a clear oil. $^1$H NMR δ5.66 (m, 2), 4.07 (d, 2, J=4 Hz), 2.03 (dd, 2, J=6, 13 Hz), 1.62 (br, 1), 1.4-1.2 (m, 14), 0.88 (t, 3, J=7 Hz).

EXAMPLE 10

Preparation of trans-2-Tetradecen-1-ol.

trans-2-Tetradecen-1-ol was prepared by reduction of the propargyl alcohol by the method described by Jones and Denmark (*Org. Syn.*, 1985, 64, 182-8) using 8.0 g (38 mmole) of 2-tetradecyn-1-ol in 30 ml of ether and 16 ml (55 mmole) of Red-Al in 40 ml of ether. Kugelrohr distillation afforded 7.67 g of clear oil. $^1$H NMR δ5.66 (m, 2), 4.08 (d, 2, J=5 Hz) 2.03 (dd, 2, J=6, 13 Hz), 1.60 (br, 1), 1.4-1.2 (m, 18), 0.88 (t, 3, J=7 HZ).

EXAMPLE 11

Preparation of ( 2S-cis)-3-Nonyloxirane methanol

To a slurry of 500 mg of powdered 4A molecular sieves in 30 ml of dry CH₂Cl₂ at 0'C. under argon, was added 232 mg (0.82 mmole) of Ti(Oi-Pr)₄ followed by 266 mg (1.14 mmole) of L(+)diisopropyl tartrate. The mixture was allowed to stir for 15 min. The mixture was cooled to −20'C and a solution of 0.75 g (4.1 mmole) of cis-2-dodecene-1-ol in 5 ml of CH₂Cl₂, which has been dried over 3A molecular sieves for 15 min, was then added. After the catalyst had "aged" for 20 min, 2.15 ml of 3.8 M (8.17 mmole) tert-butyl hydroperoxide in isooctane was added slowly by syringe. The reaction was then allowed to stand in the freezer (−30'C) for seven days. The mixture was then warmed to 0'C and 5 ml of $H_2O$ was added with stirring. After 30 min, 1.5 ml of 30% NaOH in saturated brine was added and the mixture was allowed to stir 60 min longer. The organic layer was separated and the aqueous layer was washed twice with 20 ml of $CH_2Cl_2$. The combined organic layers were dried over $MgSO_4$, filtered and evaporated to afford a sticky white solid. Recrystallization from $Et_2O$: petroleum ether yielded 570 mg of a flocculent white solid mp 55°-6° C. $^1H$ NMR (CDCl$_3$)δ3.86 (ddd, 1, J=4, 8, 12 Hz), 3.7 (m, 1), 3.16 (dt, 1, J=4, 7 Hz) 3.0 (m, 1), 1.6–1.1 (m, 12), 0.88 (t, 3, J=7 Hz). Mass spectra EI; M-31 (—CH$_2$OH), Calc. 169.1592, Found 169.1581.

EXAMPLE 12

Preparation of (2R-cis)-3-Nonyloxirane methanol.

The epoxidation was performed as described in Example 11 except that D(−)diisopropyl tartrate was used. The reaction afforded 524 mg of a white solid, mp 55°-6° C. $^1H$ NMR(CDCl$_3$) δ3.86 (ddd, 1, J=4, 8, 12 Hz), 3.7 (m, 1), 3.16 (dt, 1, J=4, 7 Hz), 3.0 (m, 1), 1.6–1.1 (m, 12), 0.88 (t, 3, J=6 Hz). Mass Spectra; EI, M-31 (—CH$_2$OH), Calc. 169.1592, Found 169.1594.

EXAMPLE 13

Preparation of (2S-cis)-3-(Benzyloxymethyl)oxirane methanol.

To a slurry of 5.0 g of powdered 4A molecular sieves in 400 ml of dry $CH_2Cl_2$ was added 2.09 g (8.42 mmole) of Ti(Oi-Pr)4 and 2.76 g (11.8 mmole) of L(+)diisopropyl tartrate at O'C under argon. The mixture was allowed to stir for 10 min, cooled to −20° C., and 22.5 ml of 3.8M tert-butyl hydroperoxide in isooctane is added slowly at −20° C. The catalyst was allowed to "age" for 30 min. A solution of 7.50 g (42.1 mmole) of Z-4-(benzyloxy)-2-buten-1-ol in 15 ml of $CH_2Cl_2$ was dried over 3A molecular sieves for 15 min and then added to the mixture at −20° C. over 10 min. The mixture was allowed to stand in a refrigerator at 2° C. for 8 days. The reaction mixture was removed from the refrigerator and 40 ml of $H_2O$ was added with stirring. After stirring for 30 min, 15 ml of 30% NaOH in saturated brine was added and the mixture was allowed to stir 60 min longer. The organic layer was separated and the aqueous layer washed twice with 50 ml of $CH_2Cl_2$. The organic layers were combined, dried over $MgSO_4$, filtered and evaporated to afford a milky, pale yellow oil. Distillation yielded 4.80 g of a clear viscous oil, bp 132°-5° C. (0.2 mm Hg). $^1H$ NMR, δ7.4–7.2 (m, 5), 4.58 (dd, 2, J=12, 20 Hz), 3.7 (m, 4), 3.27 (ddd, 2, J=5, 10, 15 Hz), 1.98 (t, 1, J=6 Hz). Mass Spectra; EI; M+, Calc. 194.0942, Found 194.0929.

EXAMPLE 14

Preparation of (2R-cis)-3-(Benzyloxymethyl)oxirane methanol.

The epoxidation was performed as described in Example 13 except with 8.0 g of powdered 4A sieves, 600 ml $CH_2Cl_2$, 3.34 g (13.5 mmole) of Ti(OiPr)4, 4.41 g (19.8 mmole) of D(-)diisopropyl tartrate, 35.5 ml of 3.8M tert-butylhydroperoxide in isooctane, and 11.98 g of (Z)-4-(benzyloxy)-2-butene-1-ol. Workup with 70 ml $H_2O$ and 25 ml NaOH/Brine afforded 8.65 g of clear oil after distillation, bp 132°-4° C. (0.1 mm Hg). $^1H$ NMR δ(CDCl$_3$) 7.4–7.2 (m, 5), 4.58 (dd, 2, J=12, 20 Hz), 3.7 (m, 4), 3.27 (ddd, 2, J=5, 10, 15 Hz), 2.17 (t, 1, J=6 Hz). Mass spectra: EI, M+, Calc. 194.0942, Found 194.0960.

EXAMPLE 15

Preparation of (2S-cis)-3-Heptyloxirane methanol.

A suspension of 3.00 g of 4A powdered molecular sieves in 60 ml of dry $CH_2Cl_2$ was cooled to 0° C. under argon. To the cooled suspension was added 1.09 g (3.80 mmole) of Ti(OiPr)4 and 1.24 g (5.32 mmole) of L(+)diisopropyl tartrate via syringe. The mixture was stirred for 15 min and cooled to −20° C. A solution of tert-butylhydroperoxide in isooctane (3.8M, 7.57 ml, 28.8 mmole) was added slowly to the mixture the catalyst allowed to "age" for 30 min at −20° C. A solution of 3.00 g (19.2 mmole) of Z-2-decen-1-ol in 10 ml of $CH_2Cl_2$ was dried over 3A molecular sieves for 15 min before being added to the mixture slowly, with stirring, at −20° C. The solution was then placed in the freezer (−30° C.) and allowed to stand for 4 days. The mixture was warmed to 0° C. and poured into a solution of 2.00 g of citric acid and 5.50 g of $FeSO_4$ in 15 Ml $H_2O$. The organic layer was separated and the aqueous layer washed twice with 20 ml of $CH_2Cl_2$. The $CH_2Cl_2$ layers were combined, dried over $MgSO_4$, filtered and evaporated to yield a sticky white solid. Recrystallization from $Et_2O$; petroleum ether afforded 1.78 g of flocculent white solid, mp 42-3'C. $[\alpha]^{25}$ −3.4' (c 1.1, CHCl$_3$); $^1H$ NMR δ3.86 (ddd, 1, J=4, 8, 12 Hz), 3.67 (ddd, 1, J=5, 7, 12 Hz), 3.16 (dt, 1, J=4, 7 Hz), 3.03 (m, 1), 1.74 (m, 1) 1.6–1.2 (m, 12), 0.88 (t, 3, J=6 Hz). Mass spectra: EI; M-31 (—CH$_2$OH), Calc. 141.1279, Found 141.1281.

EXAMPLE 16

Preparation of (2R-cis)-3-Heptyloxirane methanol.

The epoxidation was performed as described in Example 15 except that D(−)diisopropyl tartrate was used. The reaction afforded 1.70 g of flocculent white crystals, mp 40°-1° C. $^1H$ NMR (CDCl$_3$)δ3.86 (ddd, 1, J=4, 8, 12 Hz), 3.67 (ddd, 1, J=5, 7, 12 Hz), 3.16 (dt, 1, J=4, 7 Hz), 3.03 (m, 1), 1.77 (dd, 1, J=5, 7 Hz), 1.6–1.2 (m, 12), 0.88 (t, 3, J=6 Hz). Mass Spectra: EI, M-31 (—CH$_2$OH), Calc. 141.1279, Found 141.1281.

EXAMPLE 17

Preparation of (2S-cis)-3-Heptyloxymethyl)oxirane methanol.

The epoxidation was performed as described in Example 15 except that 1.06 g (4.52 mmole) of L(+) diisopropyl tartrate, 0.92 g (3.23 mmole) of Ti(OiPr)4, 6.35 ml (24.2 mmole) of 3.8M tert-butylhydroperoxide in isooctane, and 3.00 g (16.1 mmole) of Z-4-(heptyloxy)-2-buten-1-ol were used. The reaction yielded 2.76 g of white crystals following crystallization from $Et_2O$: petroleum ether, mp 50°-2° C. $[\alpha]^{25}$ −15.4' (c 1.1, CHCl$_3$); $^1H$ NMR (CHCl$_3$)δ3.9–3.4 (m, 6), 3.25 (m, 2), 2.18 (dd, 1, J=6, 7 Hz), 1.60 (m, 2), 1.29 (br, 8), 0.88 (t, 3, J=6 Hz). Mass spectra: EI; M-31 (—CH$_2$OH), Calc. 171.1384, Found 171.1378.

EXAMPLE 18

Preparation of (2R-cis)-3-(Heptyloxymethyl)oxirane methanol.

The epoxidation was performed as described in Example 15 except that D(−)diisopropyl tartrate was used. The reaction afforded 2.50 g of white crystals, mp 50°-2° C. $[\alpha]^{25}$ +13.2 (c, 1.2, CHCl$_3$); $^1$H NMR (CDCl$_3$), 3.9–3.4 (m, 6), 3.25 (m, 2), 2.14 (dd, 1, J=6, 7 Hz), 1.60 (m, 2), 1.28 (br, 8), 0.88 (t, 3, J=6 Hz). Mass spectra: EI, M-31 (—CH$_2$OH), Calc. 171.1384, Found 171.1383.

EXAMPLE 19

Preparation of (2S*-cis)-3-Undecyloxiranecarboxylic acid.

A solution of 400 mg (1.89 mmole) of Z-2-tetradecen-1-ol and 13 mg (0.04 mmole) of VO(acac)$_2$ in 50 ml of CH$_2$Cl$_2$ was prepared under argon. To this solution was added 0.74 ml (2.83 mmole) of 3.8M tert- butyl hydroperoxide in isooctane. The mixture was allowed to stir for 2 days under argon. The mixture was poured into a chilled solution of 1.00 g of FeSO$_4$ and 200 mg of citric acid in 10 ml H$_2$O. The organic layer was separated and the aqueous layer washed twice with 10 ml of CH$_2$Cl$_2$. The combined organic layers a pale yellow solid. Flash chromatography (25 mm column; 50% Et$_2$O; petroleum ether) yields 288 mg of the epoxy alcohol.

To a mixture of 3 ml CCl$_4$, 3 ml CH$_3$CN, and 4.5 ml H$_2$O was added 158 mg (0.44 mmole) of the epoxy alcohol followed by 5 mg of RuCl$_3$—H$_2$O. The mixture was stirred vigorously and 600 mg (2.63 mmole) of H$_5$IO$_6$ was added in small portions over 20 min. The mixture was allowed to stir vigorously for three hours. The reaction was then diluted with 30 ml of Et$_2$O and the organic layer separated. The aqueous layer was washed twice with 10 ml of Et$_2$O. The combined organic layers were washed with 20 ml of brine, dried over MgSO$_4$, filtered through a 2 cm pad of celite and evaporated to afford a pale grey solid. Recrystallization from Et$_2$O: Petroleum ether yielded 106 mg of white solid, mp 82°-3° C. $^1$H NMR δ3.6 (d, 1, J=5Hz), 3.2 (m, 1), 1.7-1.2 (m, 20), 0.88 (t, 3, J=6 Hz). Mass Spectra: EI; M-45 (—CO$_2$H), Calc. 197.1905, Found 197.1919.

EXAMPLE 20

Preparation of (2S*-trans)-3-Undecyloxiranecarboxylic acid.

A solution of 200 mg (0.95 mmole) of E-2-tetradecen-1-ol and 6 mg (0.02 mmole) of VO(acac)$_2$ in 25 ml of CH$_2$Cl$_2$ was prepared under argon. To this solution was added 0.38 ml (1.42 mmole) of 3.8M tert-butyl hydroperoxide in isooctane. The mixture was allowed to stir for 2 days under argon. The mixture was poured into a chilled solution of 0.50 g of FeSO$_4$ and 100 mg of citric acid in 10 ml H$_2$O. The organic layer was separated and the aqueous layer was washed twice with 10 ml of CH$_2$Cl$_2$. The combined organic layers were derived over MgSO$_4$, filtered and evaporated to afford a pale yellow solid. Flash chromatography (25 mm column; 50% Et$_2$O; petroleum ether) yielded 128 mg of the epoxy alcohol.

To a mixture of 3 ml CCl$_4$, 3 ml CH$_3$CN, and 4.5 ml H$_2$O was added 100 mg (0.32 mmole) of the epoxy alcohol followed by 5 mg of RuCl$_3$—H$_2$O. The mixture was stirred vigorously and 400 mg (1.75 mmole) of H$_5$IO$_6$ was added in small portions over 20 min. The mixture was allowed to stir vigorously for three hours. The reaction was then diluted with 30 ml of Et$_2$O and the organic layer separated. The aqueous layer was washed twice with 10 ml of Et$_2$O. The combined organic layers were washed with 20 ml of brine, dried over MgSO$_4$, filtered through a 2 cm pad of celite and evaporated to afford a pale grey solid. Recrystallization from Et$_2$O: Petroleum ether yielded 106 mg of white solid, mp 76°-7° C., $^1$H NMR δ3.29 (d, 1, J=2 Hz), 3.2 (m, 1), 1.7-1.2 (m, 20), 0.88 (t, 3, J=6 Hz). Mass Spectra: EI, M-45 (—CO$_2$H), Calc. 197.1905, Found 197.1919.

EXAMPLE 21

Preparation of (2R-cis)-3-Nonyloxiranecarboxylic acid;

Method A:

To a solution of 4 ml CH$_3$CN, 4 ml CCl$_4$, and 6 ml H$_2$O was added 20 mg (0.07 mmole) RuCl$_3$—H$_2$O and 400 mg (2.00 mmole) of (2S-cis)-nonyloxirane methanol. The solution was cooled to 0° C. and 1.37 g (6.09 mmole) of H$_5$IO$_6$ was added in small portions with vigorous stirring over 15 min. The mixture was stirred vigorously for one hour. The reaction was then poured into 30 ml of Et$_2$O and the organic layer separated. The organic layer was washed four times with 40 ml of 0.1N NaOH. The combined NaOH layers were acidified to pH 2 with conc. HCl and the aqueous layer was washed four times with 30 ml of Et$_2$O. The combined Et$_2$O layers were washed with 30 ml of H$_2$O, 30 ml of brine, dried over MgSO$_4$, filtered, and evaporated to give 340 mg of an off white solid. This residue was crystallized from Et$_2$O: petroleum ether to afford 287 mg of white powder, mp 63°-4° C. $^1$H NMR (CDCl$_3$) 3.58 (d, 1, J=5 Hz), 3.24 (dd, 1, J=5, 12 Hz), 1.7-1.6 (m, 12), 0.88 (t, 3, J=6 HZ); $[\alpha]^{25}$ +9.5'. Mass Spectra: EI, M-45 (—CO$_2$H), Calc. 169.1592, Found 169.1596.

Method B:

To a solution of 500 mg (2.50 mmole) of (2S-cis)-3-nonyloxiranemethanol in 50 ml of DMF was added 3.30 g (8.75 mmole) of pyridinium dichromate. The reaction was allowed to stir overnight under argon. The mixture was then diluted with 150 ml H$_2$O and 20 ml 0.1M HCl and washed three times with 50 ml of Et$_2$O. The combined Et$_2$O layers are dried over MgSO$_4$, filtered and evaporated to afford a white powder. This residue when crystallized from petroleum ether to afforded 268 mg of white powder, mp 62°-3° C.

EXAMPLE 22

Preparation of (2-S-cis)-3-Nonyloxiranecarboxylic acid;

The oxidation was performed as described in Example 21, Method A, except that (2R-cis)-3-nonyloxirane methanol was used. The reaction affords 270 mg of white solid, mp 63°-4° C. $^1$H NMR (CDCl$_3$) 3.58 (d, 1, J=5 Hz), 3.24 (dd, 1, J=5, 12 Hz), 1.7-1.6 (m, 12), 0.88 (t, 3, J=6 Hz). Mass Spectra: EI, M-45 (—CO$_2$H), Calc. 169.1592, Found 169.1594.

EXAMPLE 23

Preparation of (2R-cis)-3-Nonyloxiranecarboxy amide.

Method A:

A solution of 50 mg of (2R-cis)-3-nonyloxirane carboxylic acid in 10 ml of Et$_2$O was treated with a solution of CH$_2$N$_2$ in Et$_2$O (prepared from N-nitrosomethylurea) at 0° C. until the yellow color persists for 20 min. The mixture was allowed to stand for one hour and the Et$_2$O was evaporated under a stream of nitrogen. The residue was flash chromatographed (10 mm column; 40% Et$_2$O; petroleum ether) to afford a clear oil.

A portion of the oil (25 mg) was dissolved in 3 ml of MeOH and 1 ml of conc. NH$_4$OH was added with stirring. The mixture was allowed to stir for three days. The solution was then diluted with 15 ml of CHCl$_3$ and the organic layer washed three times with 5 ml of 0.1N HCl, once with half-saturated NaHCO$_3$, dried over MgSO$_4$, filtered and evaporated to yield a pale yellow oil. Flash chromatography (7 mm column; 5% MeOH:CHCl$_3$) afforded 11.2 mg of a clear oil which solidified on standing. $^1$H NMR $\delta$(CDCl$_3$) 6.09 (br, 1), 5.47 (br, 1), 3.49 (d, 1, J=5 Hz), 3.19 (dd, 1, J=6, 11 Hz), 1.7–1.2 (m, 12), 0.88 (t, 3, J=6 Hz). Mass Spectra: EI; (M+) Calc. 213.1728, Found 213.1736:FAB; (M+H+) 214.

Method B:

A solution of 300 mg (1.40 mmole) of (2R-cis)-3-nonyloxiranecarboxylic acid and 0.235 ml (170 mg, 168 mmole) of triethylamine in 30 ml of THF was prepared under argon. To this solution 210 mg (1.54 mmole) of isobutylchloroformate was added and the mixture allowed to stir for 30 min. Concentrated NH$_4$OH (2 ml) was then added and the mixture stirred for an additional 2 hours. The reaction was diluted with 75 ml of Et$_2$O, washed with 50 ml of saturated NaHCO$_3$, 30 ml of brine, dried over MgSO$_4$, filtered and evaporated to yield a white residue. This residue was flash chromatographed (25 mm column; 5% MeOH:CHCl$_3$) to afford 268 mg of a white solid, mp 91°–2° C. $^1$H NMR was identical to the material prepared by Method A. $[\alpha]^{25}$ +35.6'.

EXAMPLE 24

Preparation of (2S-cis)-3-Nonyloxiranecarboxy amide.

The amide was prepared as described in Example 23 except that (2S-cis)-3-nonyloxirane carboxylic acid was used. Method A afforded 16.6 mg of a solid after chromatography. $^1$H NMR (CDCl$_3$) indicated a compound with an identical spectrum of that of the material prepared in example 13 was present, contaminated with what appeared to be the parent acid.

Method B yielded 279 mg of white solid after chromatography, mp 85°–8° C. $^1$H NMR was the same as that of material prepared by method A. Mass Spectra: FAB; (M+H+) 214.

EXAMPLE 25

Preparation of Methyl (2R-cis)-3-(benzyloxymethyl)oxirane carboxylate.

To a solution of 10 ml CCl$_4$, 10 ml CH$_3$CH, and 15 ml of H$_2$O was added 50 mg of RuCl$_3$—H$_2$O and 1.00 g (5.16 mmole) of (2S-cis)-3-(benzyloxymethyl)oxirane methanol. The solution was cooled to 0° C. and 3.50 g (15.5 mmole) of H$_5$IO$_6$ was added in portions over 15 min with vigorous stirring. The reaction was allowed to stir vigorously for 2 hours. The mixture was poured into 100 ml of Et$_2$O, the organic layer separated and the aqueous layer washed with 20 ml of Et$_2$O. The combined organic layers were washed four times with 50 ml 0.1N NaOH. The aqueous layers were combined, acidified to pH 2, and extracted three times with 50 ml Et$_2$O. The ether layers were dried over MgSO$_4$, filtered and evaporated to yield a pale yellow residue.

The residue was dissolved in 40 ml of Et$_2$O and treated with a solution of CH$_2$N$_2$ in Et$_2$O until the yellow color persists for 30 min. The solution was allowed to stand for two hours. The Et$_2$O layer was evaporated under a stream of nitrogen and the residue flash chromatographed (25 mm column; 50% Et$_2$O: petroleum ether) to afford 460 mg of a clear oil. $^1$H NMR (CDCl$_3$)$\delta$7.4–7.2 (m, 5), 4.56 (dd, 2, J=12, 22 Hz), 3.75 (S, 3), 3.73 (dd, 2, J=1, 5 Hz), 3.57 (d, 1, J=5 Hz), 3.44 (m, 1). Mass Spectra: EI, M+222(2), 91(100), 107(81) FAB M+H+223.

EXAMPLE 26

Preparation of Methyl( 2S-cis)-3-(benzyloxymethyl)oxirane carboxylate.

The compound was prepared as described in Example 25 except at twice the scale. After chromatography 985 mg of a clear oil was obtained. $^1$H NMR (CDCl$_3$)-$\delta$7.4–7.2 (m, 5), 4.56 (dd, 2, J=12, 22 Hz), 3.75 (s, 3), 3.73 (dd, 2, J-1, 5 Hz), 3.57 (d, 1, J=5 Hz), 3.44 (m, 1). Mass Spectra: EI, (M+) Calc. 222.0891, Found 222.0901.

EXAMPLE 27

Preparation of (2R-cis)-3-(Benzyloxymethyl)oxirane carboxamide.

To a solution of 50 mg of methyl (2R-cis)-3-(benzyloxymethyl)oxirane carboxylate in 3 ml of MeOH was added 1 ml of concentrated NH$_4$OH with rapid stirring. The mixture was allowed to stir for two days. The reaction was then diluted with 20 ml of CHCl$_3$ and the organic layer separated and washed three times with 10 ml of 0.1N HCl. The combined organic layers were dried over MgSO$_4$, filtered and evaporated to yield a pale yellow residue. Flash chromatography (7 mm column, 5% MeOH: CHCl$_3$) afforded 24.2 mg of a clear oil which solidified upon standing. $^1$H NMR (CDCl$_3$) 7.4–7.2 (m, 5), 6.08 (br, 1), 5.64 (br, 1), 4.58 (dd, 2, J=12, 15 Hz), 3.8 (m, 1), 3.5–3.4 (m, 3). Mass Spectra: EI: M-41 (—CONH$_2$) Calc. 163.0758, Found 163.0745.

EXAMPLE 28

Preparation of (2S-cis)-3-(benzyloxymethyl)oxirane carboxamide.

The compound was prepared as described in Example 27 except that methyl ( 2S-cis)-3-(benzyloxymethyl)oxirane carboxylate was used. After chromatography 28.6 mg of clear oil was obtained which solidifies upon standing. $^1$H NMR indicated the product was heavily contaminated with another product, probably the acid. No further purification was attempted. Mass Spectra: EI; M-44 (—CONH$_2$), Calc. 163.0758, Found 163.0745.

EXAMPLE 29

Preparation of (2S-trans)-3-Nonyloxirane methanol

A suspension of 1.00 g of 4a powdered molecular sieves in 50 ml of dry CH$_2$Cl$_2$ was cooled to 0.° C. under argon. To the cooled suspension was added 308 mg (1.09 mmole) of Ti(OiPr)$_4$ and 356 mg (1.52 mmole) of L(+)diisopropyl tartrate via syringe. The mixture was stirred for 15 min and cooled to −20° C. A solution of tert-butylhydroperoxide in isooctane (3.8M, 4.30 ml, 16.4 mmole) was added slowly to the mixture and the catalyst was allowed to "age" for 30 min at −20° C. A solution fo 2.00 g (10.9 mmole) of E-2-dodecen-1-ol in 10 ml of $CH_2Cl_2$ was dried over 3A molecular sieves for 15 min before being added to the mixture slowly, with stirring, at −20°. The solution was then placed in the freezer (−30° C.) and allowed to stand for 24 H. The mixture was warmed to 0° C. and poured into a solution of 1.00 g of citric acid and 3.50 g of $FeSO_4$ in 15 ml $H_2O$. The organic layer was separated and the aqueous layer washed twice with 20 ml of $CH_2Cl_2$. The $CH_2Cl_2$ layers were combined, dried over $MgSO_4$, filtered and evaporated to yield a sticky white solid. Recrystallization from $Et_2O$: petroleum ether afforded 1.98 g of white solid, mp 62°-4° C. $^1H$ NMR δ3.92 (ddd, 1, J=2.5, 6, 12 Hz), 3.63 (ddd, 1, J=4, 7, 12 Hz), 2.95 (m, 2), 1.69 (dd, 1, J=7, 6 Hz), 1.6–1.2 (m, 16), 0.88 (t, 3, J=6 Hz). Mass Spectra: M-31(−$CH_2OH$)(0.4)169, M(100)55.1.

EXAMPLE 30

Preparation of (2R-trans)-3-Nonyloxirane methanol

The epoxidation was performed as described of example 29 except that D(−)diisopropyl tartrate was used. The reaction afforded 1.71 g. of white solid, mp 57°-60° C. $^1H$ NMR (CDCl$_3$) δ3.92 (ddd, 1, J=2.5, 6, 12 Hz), 3.63 (ddd, 1, J=4, 7, 12 Hz), 2.95 (m, 2), 1.69 (dd, 1, J=7, 6 Hz), 1.6–1.2 (m, 16), 0.88 (t, 3, J=6 hz). Mass Spectra: M-31(—$CH_{20}H$)(0.6)169, M(100)55.1.

EXAMPLE 31

Preparation of (2S-trans)-3-Undecyloxirane methanol

A suspension of 1.00 g of 4A powdered molecular sieves in 50 ml of dry $CH_2Cl_2$ was cooled to 0° C. under argon. To the cooled suspension was added 403 mg (1.42 mmole) of Ti(OiPr)$_4$ and 463 mg (1.98 mmole) of L(+)diisopropyl tartrate via syringe. The mixture was stirred for 15 min and cooled to −20° C. A solution of tert-butylhydroperoxide in isooctane (3.8M, 5.58 ml, 21.2 mmole) was added slowly to the mixture and the catalyst was allowed to "age" for 30 min at −20° C. A solution of 3.00 g (14.2 mmole) of E-2-tetradecen-1-ol in 10 ml of $CH_2Cl_2$ was dried over 3A molecular sieves for 15 min before being added to the mixture slowly, with stirring, at −20° C. The solution was then placed in the freezer (−30° C.) and allowed to stand of 24 H. The mixture was warmed to 0° C. and poured into a solution of 1.00 g of citric acid and 5.00 g of $FeSO_4$ in 15 ml $H_2O$. The organic layer was separated and the aqueous layer washed twice with 20 ml of $CH_2Cl_2$. The $CH_2Cl_2$ layers are combined, dried over $MgSO_4$, filtered and evaporated to yield a sticky white solid. Recrystallization from $Et_2O$: petroleum ether afforded 2.34 g of white solid, mp 68°-70° C. $^1H$ NMR δ3.92 (ddd, 1, J=2.5, 6, 12 Hz), 3.63 (ddd, 1, J=4, 7, 12 Hz), 2.95 (m, 2), 1.64 (dd, 1, J=7, 5 Hz), 1.6–1.2 (m, 20), 0.88 (t, 3, J=5 Hz). Mass Spectra: M-31(−$CH_2O$ H)(1.0)197.2, M(100)55.1.

EXAMPLE 32

Preparation of (2R-trans)-3-Undecyloxirane methanol

The epoxidation was performed as described of example 31 except that D(−)diisopropyl tartrate was used. The reaction afforded 2.11 g of white solid, mp 66°-8° C. $^1H$ NMR δ3.92 (ddd, 1, J=2.5, 6, 12 Hz), 3.63 (ddd, 1, J=4, 7, 12 Hz), 2.95 (m, 2), 1.67 (dd, 1, J=7, 4Hz), 1.6–1.2 (m, 20), 0.88 (t, 3, J=5 Hz). Mass Spectra: M-31(-$CH_2O$ H)(1.0)197.2, M(110)55.1.

EXAMPLE 33

Preparation of (2S-trans)-3-heptyloxirane methanol

A suspension of 2.00 g of 4A powdered molecular sieves in 50 ml of dry $CH_2Cl_2$ was cooled to 0° C. under argon. To the cooled suspension was added 273 mg (1.00 mmole) of Ti(OiPr)4 and 314 mg (1.34 mmole) of L(+)diisopropyl tartrate via syringe. The mixture was stirred for 15 min and cooled to −20° C. A solution of tert-butylhydroperoxide in isooctane (3.8M, 7.57 ml, 28.8 mmole) was added slowly to the mixture and the catalyst was allowed to "age" for 30 min at −20° C. A solution of 3.00 g (19.2 mmole) of E-2-decen-1-ol in 10 ml of $CH_2Cl_2$ was dried over 3A molecular sieves for 15 min before being added to the mixture slowly, with stirring, at −20° C. The solution was then placed in the freezer (−30° C.) and allowed to stand for 24 H. The mixture was warmed to 0° C. and poured into a solution of 1.00 g of citric acid and 5.00 g of $FeSO_4$ in 15 ml $H_2O$. The organic layer was separated and the aqueous layer washed twice with 20 ml of $CH_2Cl_2$. The $CH_2Cl_2$ layers are combined, dried over $MgSO_4$, filtered and evaporated to yield a sticky white solid. Recrystallization from $Et_2O$: petroleum ether afforded 2.43 g of white solid, mp 50°-1° C. $^1H$ NMR δ3.92 (ddd, 1, J=2, 6, 12 Hz), 3.63 (ddd, 1, J=4, 8, 12 Hz), 2.94 (m, 2), 1.73 (dd, 1, J=6, 7 Hz), 1.6–1.2 (m, 12), 0.88 (t, 3, J=7 Hz). Mass Spectra: M-31(-$CH_2O$ H)(0.5)148.1, M(100)69.1.

EXAMPLE 34

Preparation of (2R-trans)-3-Heptyloxirane methanol

The epoxidation was performed as described of example 33 except that D(−)diisopropyl tartrate was used. The reaction afforded 2.72 g of white solid, mp 48°-50° C. $^1H$ NMR (CDCl$_3$) δ3.92 (ddd, 1, J=2, 6, 12 hz), 3.63 (ddd, 1, J=4, 8, 12 Hz), 2.94 (m, 2), 1.70 (dd, 1, J=6, 7 hz), 1.6–1.2 (m, 12), 0.88 (t, 3, J=7 Hz). Mass Spectra: M-31(-$CH_2O$ H)(0.5)141.1, M(100)69.1.

EXAMPLE 35

Preparation of (2R-trans)-3-Nonyloxiranecarboxylic acid

To a solution of 2 ml $CH_3CN$, 2 ml $CCl_4$, and 3 ml $H_2O$ was added 13 mg 90.05 mmole) $RuCl_3$—$H_2O$ and 500 mg 92.50 mmole) of (2S-trans)-nonyloxirane methanol. The solution was cooled to 0° C. and 1.43 g (6.25 mmole) of $H_5IO_6$ was added in small portions with vigorous stirring over 15 min. The mixture was stirred vigorously for one hour. The reaction was then poured into a mixture of 30 ml of $Et_2O$ and 10 ml of N HCl and the organic layer was separated. The aqueous layer was washed three times with 30 ml of ether. The combined $Et_2O$ layers were washed with 30 ml of $H_2O$, 30 ml of brine, dried over $MgSO_4$, filtered, and evaporated to give 340 mg of an off white solid. The residue was filtered through a three inch pad of silica with ether and crystallized from $Et_2O$: petroleum ether to afford 293 mg of white powder, mp 56°-7° C. $^1H$ NMR (CDCl$_3$) δ3.27 (d, 1, J=2 hz), 3.19 (dt, 1, J=2, 6 Hz), 3.19 (dt, 1, J=2, 6 Hz), 1.6–1.2 (m, 16), 0.88 (t, 3, J=6 Hz). Mass Spectra: M-45(—$CO_2H$)(2.2)169.1, M(100)41.0.

EXAMPLE 36

Preparation of (2S-trans)-3-Nonyloxiranecarboxylic acid

Method A:

To a solution of 2 ml $CH_3CN$, 2 ml $CCl_4$, and 3 ml $H_2O$ was added 13 mg (0.04 mmole) $RuCl_3$—$H_2O$ and 400 mg (2.00 mole) of (2R-trans)-nonyloxirane methanol. The solution was cooled to 0° C. and 1.14 g (5.00 mmole) of $H_5IO_6$ was added in small portions with vigorous stirring over 15 min. The mixture was stirred vigorously for one hour. The reaction was then poured into 30 ml of $Et_2O$ and 10 ml of 1 n HCl and the organic layer was separated. The aqueous layer was washed three times with 30 ml of ether. The combined $Et_2O$ layers were washed with 30 ml of $H_2O$, 30 ml of brine, dried over $MgSO_4$, filtered, and evaporated to give 340 mg of an off white solid. This residue was filtered through a three inch pad of silica with other and crystallized from $Et_2O$: petroleum ether to afford 220 mg of white powder, mp 55°-8° C. $^1H$ NMR ($CDCl_3$) δ3.27 (d, 1, J=2 Hz), 3.18 (dt, 1, J=2, 6 Hz), 1.6-1.2 (m, 16), 0.88 (t, 3, J=6 Hz). Mass Spectra: M-45(—$CO_2H$)(2.2)167.1, M(100)41.0.

Method B:

To a solution of 300 mg (1.50 mmole) of (2R-trans)-3-nonyloxiranemethanol in 50 ml of DMF was added 3.50 (9.31 mmole) of pyridinium dichromate. The reaction was allowed to stir overnight under argon. The mixture was then diluted with 150 ml $H_2O$ and 20 ml 0.1M HCl and washed three times With 50 ml of $Et_2O$. The combined $Et_2O$ layers are dried over $MgSO_4$, filtered and evaporated to afford a white powder. This residue was crystallized from petroleum ether to afford 268 mg of white power, mp 62°-3° C.

EXAMPLE 37

Preparation of (2R-cis)-3-Heptyloxirane carboxylic acid.

To a solution of 300 mg (1.16 mmole) (2R-cis)-3-heptyloxiranemethanol in 50 ml of DMF was added 2.62 g (6.97 mmole) of pyridinium dichromate. The reaction was allowed to stir overnight under argon. The mixture was then diluted with 150 ml $H_2O$ and 20 ml 0.1M HCl and washed three times with 50 ml of $Et_2O$. The combined $Et_2O$ layers are dried over $MgSO_4$, filtered and evaporated to afford a white powder. This residue was crystallized from petroleum ether to afford 155 mg of white power, mp 53°-5° C. $^1H$ NMR ($CDCl_3$) δ3.60 (d, 1, J=5 Hz), 3.24 (dd, 1, J=5 12 Hz), 1.6-1.2 (m, 12), 0.88 (t, 3, J=7 Hz). Mass Spectra: M-45(—$CO_2H$)(3.7)141.1, M(100)41.0.

EXAMPLE 38

Preparation of (2S-cis)-3-Heptyloxiranecarboxylic acid

To a solution of 500 mg (2.50 mmole) of (2R-cis)-3-heptyloxiranemethanol in 50 ml of DMF was added 3.30 g (8.75 mmole) of pyridinium dichromate. The reaction was allowed to stir overnight under argon. The mixture was then diluted with 150 ml $H_2O$ and 20 ml 0.1M HCl and washed three times with 50 ml of $Et_2O$. The combined $Et_2O$ layers were dried over $MgSO_4$, filtered and evaporated to afford a white powder. This residue was crystallized from petroleum ether to afford 39 mg of white power, mp 62°-3° C. $^1H$ NMR ($CDCl_3$) δ3.59 (d, 1, J=5 Hz), 3.24 (m, 1), 1.6-1.2 (m, 12), 0.88 (t, 3, J=7 Hz). Mass Spectra: M+(19.1)186.1, M-45(42.3)141.1, M(100)95.1.

EXAMPLE 39

Preparation of (2R-trans)-3-Undecyloxiranecarboxylic acid

To a solution of 4 ml $CH_3CN$, 4 ml $CCl_4$, and 6 ml $H_2O$ was added 20 mg (0.07 mmole0 $RuCl_3$—$H_2O$ and 400 mg (2.00 mmole) of (2S-trans)-undecyloxirane methanol. The solution was cooled to 0° C. and 1.37 g (6.09 mmole) of $H_5IO_6$ was added in small portions with vigorous stirring over 15 min. The mixture was stirred vigorously for one hour. The reaction was then poured into 30 ml of $Et_2O$ and 10 ml of 1 H HCl and the organic layer was separated. The aqueous layer was washed three times with 30 ml of ether. The combined $Et_2O$ layers were washed with 30 ml of $H_2O$, 30 ml of brine, dried over $MgSO_4$, filtered, and evaporated to giue an off-white solid. This residue was filtered through a three inch pad of silica with ether and crystallized from $Et_2O$: petroleum ether to afford 240 mg of white powder, mp 66°-8° C. $^1H$ NMR ($CDCl_3$)δ3.27 (d, 1, J=2 Hz), 3.19 (dt, 1, J=2, 6 Hz), 1.6-1.2 (m, 20), 0.88 (t, 3, J=7 Hz). Mass Spectra: M+(0.7)212.2, M-45(5.5)197.2, M(100)41.0.

EXAMPLE 40

Preparation of (2S-trans)-3-Undecyloxiranecarboxylic acid

The reaction was performed as described for example 39 except that (2R-trans)-undecyloxirane methanol was used. After workup and crystallization from $Et_2O$: petroleum ether the reaction afforded 335 mg of white powder, mp 75°-7° C. $^1H$ NMR ($CDCl_3$)δ3.27 (d, 1, J=2 Hz), 3.19 (dt, 1, J=2, 6 Hz), 1.6-1.2 (m, 20), 0.88 (t, 3, J=7 Hz). Mass Spectra: M+(1.2)242.2, M-45(10.8)197.2, M(100)41.0.

EXAMPLE 41

Preparation of N-(2R-cis)-3-Nonyloxiraneacyl L-proline methyl ester

A solution of 50 mg (0.23 mmole) of (2R-cis)-3-nonyloxiranecarboxylic acid and 0.101 ml (71 mg, 0.70 mmole) of triethylamine in 5 ml of THF was prepared under argon and cooled to 0° C. To this solution 33 mg (0.24 mmole) of isobutylchloroformate was added and the mixture was allowed to stir for 30 min. L-Proline methyl ester hydrochloride (50 mg, 0.30 mmole) was then added and the mixture was stirred for an additional 2 hours. The reaction was diluted with 75 ml of $Et_2O$, washed with 50 ml of saturated $NaHCO_3$, 30 ml of brine, dried over $MgSO_4$, filtered and evaporated to yield a white residue. This residue was flash chromatographed (25 mm column; 5% MeOH:$CHCl_3$) to afford 60 mg of a-clear oil. $^1H$ NMR reveals the oil to be a mixture of the cis- and trans-amide isomers (ca. 1:2 ratio). $^1H$ NMR (trans) 4.55 (m, 1), 3.72 (s, 3), 3.58 (d, 1, J=4); (cis) 4.82 (dd, 1, J=4, 8 Hz), 3.77 (s, 3), 3.52 (d, 1, J=4 Hz);(cis and trans) 3.18 (m, 1), 2.4-1.8 (m, 4), 1.6-1.2 9m, 18), 0.8S (t, 3, J=7 Hz). Mass Spectra: M+(0.5)325.2, M—$CO_2Me$(8.7)266.2, M(100)70.1.

EXAMPLE 42

Preparation of N,N-Diethyl-(2R-cis)-3-nonyloxiranecarboxy amide

A solution of 75 mg 90.35 mmole) of (2R-cis)-3-nonyloxiranecarboxylic acid and 0.148 ml (106 mg, 1.05 mmole) of triethylamine in 5 ml of THF was prepared under argon and cooled to 0° C. To this solution 50 mg (0.37 mmole) of isobutylchloroformate was added and the mixture was allowed to stir of 30 min. Diethylamine (0.109 ml, 76 mg, 1.05 mmole) was then added and the mixture stirred for an additional 2 hours. The reaction was diluted with 75 ml of Et$_2$O, washed with 50 ml of saturated NaHCO$_3$, 30 ml of brine, dried over MgSO$_4$, filtered and evaporated to yield a clear residue. This residue was flash chromatographed (25 mm column; 5% MeOH:CHCl$_3$) to afford 80 mg of a clear oil. $^1$H NMR 3.57 (d, 1, J=4 Hz), 3.6-3.3 (m, 4), 3.2 (m, 1), 1.6-1.2 (m, 19), 1.13 (t, 3, J=7 Hz), 0.88 (t, 3, J=7 Hz). Mass Spectra: M+(1.5)269, M-OH(1.3)252, M(100)100.1.

EXAMPLE 43

Preparation of cis-2-Epoxydecene

A solution of 2.00 g (14.3 mmole) of cis-2-decene in 70 ml of CH$_2$Cl$_2$ was prepared and 3.40 g (15.7 mmole) of ca. 80% MCPBA was added in one portion. The solution became slightly warm and was allowed to stir overnight. The m-chlorobenzoic acid which had precipitated was removed by filtration and the filtrate was washed twice with 100 ml of 1N NaOH. The organic layer was dried over MgSO$_4$, filtered and the solvent evaporated to give a clear oil. After kugelrohr distillation (50°-60° C. oven, 0.2 mm) 1.836 g of a clear oil was obtained. $^1$H NMR δ3.04 (ddd, 1, J=4, 5, 10), 2.90 (m, 1), 1.6-1.1 (m, 15), 0.88 (t, 3, J=7 Hz).

In-vitro screening anti-HIV XTT assay

This assay, which is available to the public by the National Cancer Institute, utilizes colorimetry based on the production of a colored formazin from a tetrazolium salt by viable cells, to develop a safe, rapid and quantitative measure of HIV cytopathology. The assay is a modification of the previously described screening method for the detection of anti-tumor drug cytotoxicity (D. A. Scudiero, et al, *Cancer Res*, 48, 4827-4833 (1988)). It involves the plating of susceptible human "host" cells with and without virus in microculture plates, adding various concentrations of the respective test compounds, incubating the plates for seven days, during which time infected, non-drug treated control cells are largely or totally destroyed by the virus. The number of remaining viable cells are determined utilizing a colorimetric endpoint. The results are summarized in Table 1 which appears below. A beneficial antiviral effect is indicated by a response % greater than the virus kill %, with 100% being optimal.

TABLE 1

| Compound of Example | RUN | Dose ug/ml | Antiviral Effect | Virus Source | Virus Kill |
|---|---|---|---|---|---|
| 11 | 1 | 10 | 60.2% | C | 6.0% |
| | 2 | 1 | 37.5% | C | 25.0% |
| | 3 | 23 | 19.9% | C | 14.0% |
| | 4 | 11.5 | 18.1% | C | 12.5% |
| | 5 | 31.9 | 23.9% | C | 13.0% |
| | 6 | 11.5 | 12.3% | C | 9.0% |
| | 7 | 31.9 | 13% | C | 11.0% |
| | 8 | 10 | 110% | V | 25.0% |
| | 9 | 23 | 30% | V | 23.0% |
| | 10 | 11.5 | 68.5% | V | 49.0% |
| | 11 | 31.9 | 65.1% | V | 53.0% |
| | 12 | 11.5 | 80.4% | V | 30.0% |
| | 13 | 31.9 | 82.6% | V | 22.0% |
| | 14 | 3.9 | 21.5% | V | 20.0% |
| | 15* | 3.9 | 32.4% | V | 25.0% |
| 21 | 1 | 1 | 18.9% | C | 9.0% |
| | 2 | 10 | 27.3% | C | 22.0% |
| | 3 | 6.3 | 16.6% | C | 12.0% |
| | 4 | 31.5 | 19.6% | C | 14.0% |
| | 5 | 24.6 | 21.6% | C | 14.0% |
| | 6 | 31.5 | 10.7% | C | 12.0% |
| | 7 | 24.6 | 13% | C | 18.0% |
| | 8 | 10 | 94% | V | 23.0% |
| | 9 | 6.3 | 25.7% | V | 19.0% |
| | 10 | 31.5 | 75.3% | V | 53.0% |
| | 11 | 24.6 | 64.3% | V | 57.0% |
| | 12 | 31.5 | 62% | V | 27.0% |
| | 13 | 24.6 | 88% | V | 40.0% |
| | 14 | 27.2 | 25.7% | V | 18.0% |
| | 15* | 27.2 | 28.1% | V | 25.0% |
| 23 | 1 | 28 | 75.6% | C | 6.0% |
| | 2 | 76 | 28.5% | C | 17.0% |
| | 3 | 38 | 35.1% | C | 14.0% |
| | 4 | 140 | 25.1% | C | 14.0% |
| | 5 | 38 | 17% | C | 17.0% |
| | 6 | 14 | 16% | C | 17.0% |
| | 7 | 2.8 | 108% | V | 19.0% |
| | 8 | 7.6 | 40.2% | V | 30.0% |
| | 9 | 3.8 | 60.1% | V | 52.0% |
| | 10 | 14 | 60.1% | V | 52.0% |
| | 11 | 380 | 24% | V | 20.0% |
| | 12 | 140 | 31% | V | 20.0% |
| | 13* | 27 | 79.6% | V | 22.0% |
| 12 | 1 | 10 | 75.1% | C | 6.0% |
| | 2 | 10 | 71.3% | C | 27.0% |
| | 3 | 50 | 32.1% | C | 16.0% |
| | 4 | 4.9 | 31.6% | C | 16.0% |
| | 5 | 2.9 | 23.1% | C | 15.0% |
| | 6 | 4.9 | 16.7% | C | 11.0% |
| | 7 | 29 | 15.7% | C | 11.0% |
| | 8 | 50 | 56.9% | V | 27.0% |
| | 9 | 4.9 | 82.4% | V | 53.0% |
| | 10 | 2.9 | 82.9% | V | 55.0% |
| | 11 | 49 | 54.9% | V | 30.0% |
| | 12 | 2.9 | 62.2% | V | 36.0% |
| | 13 | 21 | 53.4% | V | 19.5% |
| | 14 | 21 | 98.7% | V | 24.0% |
| 22 | 1 | 10 | 50.1% | C | 21.0% |
| | 2 | 0.1 | 25.6% | C | 20.0% |
| | 3 | 0.1 | 9.5% | C | 8.0% |
| | 4 | 34.6 | 25.9% | C | 16.0% |
| | 5 | 29 | 18.5% | C | 13.0% |
| | 6 | 34.6 | 12.8% | C | 14.0% |
| | 7 | 2.9 | 11.5% | C | 16.0% |
| | 8 | 34.6 | 85.5% | V | 54.0% |
| | 9 | 29 | 68.5% | V | 55.0% |
| | 10 | 34.6 | 40.3% | V | 26.0% |
| | 11 | 29 | 41.9% | V | 33.0% |
| | 12 | 24.8 | 23.1% | V | 30.0% |
| | 13* | 24.8 | 26.6% | V | 20.0% |
| 24 | 1 | 35.2 | 73% | C | 16.0% |
| | 2 | 20.7 | 67.4% | C | 16.0% |
| | 3 | 3.52 | 11.3% | C | 9.0% |
| | 4 | 2.07 | 10.5% | C | 9.0% |
| | 5 | 35.2 | 73% | V | 54.6% |
| | 6 | 20.7 | 71.4% | V | 54.6% |
| | 7 | 3.52 | 28.1% | V | 26.0% |
| | 8 | 20.7 | 34% | V | 26.0% |
| | 9 | 1.34 | 41.7% | V | 20.0% |
| | 10* | 0.135 | 114% | V | 23.0% |
| 13 | 1 | 0.1 | 22.1% | C | 21.0% |
| | 2 | 1 | 15.7% | C | 13.0% |
| | 3 | 1 | 10.2% | C | 11.0% |
| | 4 | 0.1 | 50% | V | 55.0% |
| | 5 | 0.1 | 52.5% | V | 27.0% |
| | 6 | 4.4 | 28.4% | V | 24.0% |
| | 7* | 0.44 | 30.1% | V | 27.0% |

TABLE 1-continued

| Compound of Example | RUN | Dose ug/ml | Antiviral Effect | Virus Source | Virus Kill |
|---|---|---|---|---|---|
| 25 | 1 | 100 | 28.6% | C | 20.0% |
|  | 2 | 100 | 19.5% | C | 13.0% |
|  | 3 | 10 | 12.3% | C | 11.0% |
|  | 4 | 10 | 46.5% | V | 55.0% |
|  | 5 | 1 | 49% | V | 27.0% |
|  | 6 | 4.7 | 25.6% | V | 22.0% |
|  | 7* | 4.7 | 28.5% | V | 22.0% |
| 14 | 1 | 0.1 | 21.9% | C | 18.0% |
|  | 2 | 10 | 53.5% | C | 17.0% |
|  | 3 | 10 | 61% | C | 17.0% |
|  | 4 | 0.1 | 12.1% | C | 10.0% |
|  | 5 | 10 | 10.5% | C | 10.0% |
|  | 6 | 1 | 43.5% | V | 50.0% |
|  | 7 | 10 | 49.5% | V | 50.0% |
|  | 8 | 0.1 | 17.7% | V | 16.0% |
|  | 9 | 0.1 | 20.6% | V | 16.0% |
|  | 10 | 4.1 | 28.8% | V | 29.0% |
|  | 11* | 0.004 | 30% | V | 25.0% |
| 26 | 1 | 10 | 20.8% | C | 17.0% |
|  | 2 | 10 | 39.4% | C | 13.2% |
|  | 3 | 100 | 54% | C | 13.2% |
|  | 4 | 10 | 13.8% | C | 12.0% |
|  | 5 | 100 | 16.3% | C | 12.0% |
|  | 6 | 10 | 58.7% | V | 54.0% |
|  | 7 | 100 | 81.3% | V | 54.0% |
|  | 8 | 1 | 19.8% | V | 23.0% |
|  | 9 | 100 | 23.7% | V | 23.0% |
|  | 10 | 487 | 28.1% | V | 30.0% |
|  | 11* | 0.487 | 26.6% | V | 25.0% |
| 19 | 1 | 1 | 22.6% | C | 21.0% |
|  | 2 | 10 | 55.7% | C | 15.0% |
|  | 3 | 1 | 11.6% | C | 13.0% |
|  | 4 | 10 | 63.9% | V | 57.0% |
|  | 5 | 10 | 38.8% | V | 26.0% |
|  | 6 | 0.1 | 27.6% | V | 19.0% |
|  | 7* | 1 | 12.5% | V | 25.0% |
| 20 | 1 | 10 | 22.6% | C | 18.0% |
|  | 2 | 10 | 59.5% | C | 14.0% |
|  | 3 | 100 | 60.9% | C | 14.0% |
|  | 4 | 100 | 10% | C | 10.0% |
|  | 5 | 100 | 10.2% | C | 10.0% |
|  | 6 | 100 | 75.7% | V | 55.0% |
|  | 7 | 100 | 84.3% | V | 55.0% |
|  | 8 | 100 | 40.2% | V | 24.0% |
|  | 9 | 100 | 72.5% | V | 24.0% |
|  | 10 | 4.07 | 45.5% | V | 25.0% |
|  | 11* | 4.07 | 87.4% | V | 23.0% |
| 15 | 1 | 46 | 58.3% | C | 15.0% |
|  | 2 | 4.6 | 11.8% | C | 13.0% |
|  | 3 | 92 | 60.8% | V | 35.0% |
|  | 4 | 10 | 78.2% | V | 57.0% |
|  | 5 | 10 | 58.6% | V | 26.0% |
|  | 6* | 21.6 | 32% | V | 31.0% |
| 16 | 1 | 10.6 | 27.3% | C | 14.0% |
|  | 2 | 80.2 | 69.6% | C | 15.0% |
|  | 3 | 80.2 | 84.5% | C | 15.0% |
|  | 4 | 160 | 62.6% | V | 40.0% |
|  | 5 | 80.2 | 97.3% | V | 60.0% |
|  | 6 | 80.2 | 88.6% | V | 30.0% |
|  | 7 | 23.8 | 35.9% | V | 22.0% |
|  | 8* | 23.8 | 39.7% | V | 28.0% |
| 17 | 1 | 113 | 31.1% | C | 10.0% |
|  | 2 | 56.7 | 53.7% | C | 15.0% |
|  | 3 | 56.7 | 83.1% | C | 15.0% |
|  | 4 | 11.3 | 57.6% | V | 40.0% |
|  | 5 | 56.7 | 102% | V | 57.0% |
|  | 6 | 56.7 | 69.2% | V | 26.0% |
|  | 7* | 1.97 | 15.8% | V | 28.0% |
| 18 | 1 | 96.5 | 38.6% | C | 11.0% |
|  | 2 | 48.4 | 30.7% | C | 16.0% |
|  | 3 | 4.84 | 17% | C | 10.0% |
|  | 4 | 9.65 | 58.8% | V | 40.0% |
|  | 5 | 48.4 | 89.8% | V | 63.0% |
|  | 6 | 48.4 | 49% | V | 26.0% |
|  | 7 | 2.4 | 29.4% | V | 20.0% |
|  | 8* | 2.4 | 40.2% | V | 25.0% |

Anti-viral effect: Response (Viable Cells, determined by colorometric absorbance of formazan dye produced) as % of uninfected controls
Virus Source: HIV-1 IIIb; C, Virus producing H9 cells; V, cell free virus
Virus Kill: Infected untreated cells as % of uninfected cell controls
*Culture redosed with compound after 3 days

Activity against HIV Protease

The assay for proteolyic activity is a modified version of that previously described by Copeland et al., Gene Anal. Tech., 5:109–115 (1988). For each assay to be performed 2 microliters of protease solution (ca. 100 ng) is added to 3 μg of nonapeptide (Val-Ser-Gln-Asn-Tyr-Pro-Ile-Val-Gln-$NH_2$) in 8 μl of 200 mM sodium phosphate, 1M NaCl, 5% glycerol, 0.25% Nonidet-40, at pH 6.5. This affords a stock solution containing 10 μl per number of reactions. This stock is aliquoted out in 10 μl portions to which 0.5 μl of DMSO (a control is run with each set of assays to compensate for minor experimental variations) or a DMSO solution containing 10 μg/μl of an inhibitor, i.e., any one of the compounds of the present invention, is added. The reactions were incubated at room temperature and 4 μl portions were removed at ca. 16 and 40 hr. intervals. HPLC analysis was performed on a 4.6×250 mm Lichrosorb RP-18 column eluted with a gradient of 0–40% acetonitrile in water (containing 0.05% TFA) over 30 min monitoring absorbance at 206 nm. Progress of the enzymatic cleavage was followed by monitoring the appearance of the pentapeptide (Val-Ser-Gln-Asn-Tyr-OH) cleavage product. The activity is expressed as the amount of the pentapeptide (Val Ser-Gln-Asn-Tyr-OH) observed relative to the control reaction for that set of assays. The results are reported in Table 2 below.

TABLE 2

Inhibition of HIV-2 Protease

| Example # | Compound | Percent Control Cleavage of Nonapeptide HIV-1 Cleavage Site Fragment |
|---|---|---|
|  | Myristic Acid | 111% |
|  | Cerulenin | 10% |
|  | Pepstatin A | 1% |
|  | 1,2-Epoxy-3-(p-nitrophenoxy)propane | 18% |
| 3 | cis-2-Decenol | 105% |
| 12 | 2R-cis-Nonyloxirane methanol | 96% |
| 11 | 2S-cis-Nonyloxirane methanol | 85% |
| 16 | 2R-cis-Heptyloxirane methanol | 42% |
| 15 | 2S-cis-Heptyloxirane methanol | 59% |
| 18 | 2R-cis-(Heptyloxymethyl)oxirane methanol | 71% |
| 17 | 2S-cis-(Heptyloxymethyl)oxirane methanol | 66% |
| 19 | 2-cis-Undecyloxirane methanol | 104% |
| 14 | 2R-cis-(Benzyloxymethyl)oxirane methanol | 78% |
| 13 | 2S-cis-(Benzyloxymethyl)oxirane methanol | 81% |
| 43 | cis-2-Epoxydecene | 102% |
| 30 | 2R-trans-Nonyloxirane methanol | 105% |
| 29 | 2S-trans-Nonyloxirane methanol | 106% |
| 34 | 2R-trans-Heptyloxirane methanol | 104% |
| 33 | 2S-trans-Heptyloxirane methanol | 105% |
| 32 | 2R-trans-Undecyloxirane methanol | 98% |
| 31 | 2S-trans-Undecyloxirane methanol | 95% |
| 20 | 2-trans-Undecyloxirane methanol | 88% |
| 21 | 2R-cis-Nonyloxiranecarboxylic acid | 56% |
| 22 | 2S-cis-Nonyloxiranecarboxylic acid | 60% |
| 37 | 2R-cis-Heptyloxiranecarboxylic acid | 104% |

TABLE 2-continued

Inhibition of HIV-2 Protease

| Example # | Compound | Percent Control Cleavage of Nonapeptide HIV-1 Cleavage Site Fragment |
|---|---|---|
| 38 | 2S-cis-Heptyloxiranecarboxylic acid | 105% |
| 19 | 2-cis-Undecyloxiranecarboxylic acid | 77% |
| 35 | 2R-trans-Nonyloxiranecarboxylic acid | 77% |
| 36 | 2S-trans-Nonyloxiranecarboxylic acid | 12% |
| 39 | 2R-trans-Undecyloxiranecarboxylic acid | 84% |
| 40 | 2S-trans-Undecyloxirane carboxylic acid | 93% |
| 23 | 2R-cis-Nonyloxiranecarboxy amide | 102% |
| 24 | 2S-cis-Nonyloxiranecarboxy amide | 113% |
|  | Cerulenin | 10% |
| 42 | N,N-Diethyl-2R-cis-nonloxiranecarboxy amide | 77% |
| 41 | N-(2R-cis-Nonyloxiraneacyl)-L-proline methyl ester | 24% |

Renin Activity: Porcine Renin Cleavage of Porcine Tetradecapeptide

Proteolytic enzymes are ubiquitous in many living systems. Renin is an asparxyl protease found in mammals which is responsible for the regulation of blood pressure. Structural and functional similarities between Renin and retroviral proteases have been previously noted (Pearl, L. H., Taylor, W. R., (1987) Nature, 329, 351–354). Consequently, successful therapeutic inhibition of retroviral proteases depends on the ability of the inhibitor to inhibit the retroviral enzyme while having a greatly diminished effect on normally occurring enzymes like Renin. The failure to inhibit the desired enzyme selectively may have an adverse effect on normal biochemical functions. The similarity of Renin to retroviral proteases and its viral normal bodily function makes it an attractive system in which to examine inhibitory selectivity.

Renin activity was determined by a method similar to that described above for the HIV protease. A solution containing 0.37 m unit (0.5 μl of stock solution containing 0.75 m unit/μl) of porcine Renin (Sigma) was added to 5 μg of porcine angiotensinogen in 5 μl of 0.1M citrate-phosphate buffer (pH 6.00) containing 0.25% NP-40. A DMSO solution containing the inhibitor (0.5 μl of a 5 μg/μl solution) was added and the reaction was allowed to incubate at room temperature for 70 min. The entire mixture was analyzed by HPLC. Chromatographic analysis was performed on a 4.6×250 mm Lichrosorb RP-18 column eluting with a gradient of 0–50% acetonitrile in 0.02M KH$_2$PO$_4$ (pH 4.7) over 30 min monitoring absorbance at 206 nm. Appearance of both the tetrapeptide and the decapeptide products may be monitored under these conditions. Enzyme activity is expressed as the amount of tetrapeptide produced relative to an uninhibited control, and are summarized in Table 3 below.

TABLE 3

| Compound of Example | Compound | Percent control (tetrapeptide produced) |
|---|---|---|
| 35 | 2R-trans-Nonyloxirane-carboxylic acid | 72% |
| 36 | 2S-trans-Nonyloxirane-carboxylic acid | 12% |
| 39 | 2R-trans-Undecyloxirane-carboxylic acid | 51% |
| 40 | 2S-trans-Undecyloxirane-carboxylic acid | 71% |
| 21 | 2R-cis-Nonyloxiranecarboxylic acid | 86% |
| 15 | 2S-cis-Heptyloxirane methanol | 86% |
| 16 | 2R-cis-Heptyloxirane methanol | 96% |
| 11 | 2S-cis-Nonyloxirane methanol | 106% |
| 23 | 2R-cis-Nonyloxiranecarboxylic amide | 88% |
| 24 | 2S-cis-Nonyloxiranecarboxylic amide | 106% |
|  | Cerulenin | 68% |
|  | Epoxy-3-(p-nitrophenoxy)propene | 106% |
|  | Pepstatin A | 0% |

The compounds of the present invention may be made into pharmaceutical compositions by combination with appropriate pharmaceutically acceptable carriers or diluents, and may be formulated into preparations in solid, semisolid, liquid or gaseous forms such as tablets, capsules, powders, granules, ointments, solutions, suppositories, injections, inhalants, and aerosols in the usual ways for their respective route of administration. The following methods and excipients are merely exemplary and are in no way limiting.

In pharmaceutical dosage forms, the compounds of the present invention may be used in the form of their pharmaceutically acceptable salts, and also may be used alone or in appropriate association, as well as in combination with other pharmaceutically active compounds.

In the case of oral preparations, the compounds may be used alone or in combination with appropriate additives to make tablets, powders, granules or capsules, e.g., with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl- cellulose; with lubricants such as talc or magnesium stearate; and if desired, with diluents, buffering agents, moistening agents, preservatives and flavoring agents.

Furthermore, the compounds of the present invention may be made into suppositories by mixing with a variety of bases such as emulsifying bases or water-soluble bases.

The compounds of the present invention may be formulated into preparations for injections by dissolving, suspending or emulsifying them in an aqueous or non-aqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In the cases of inhalations or aerosol preparations, the compounds of the invention in the form of a liquid or minute powder may be filled up in an aerosol container with gas or liquid spraying agents, and if desired, together with conventional adjuvants such as humidifying agents. They may also be formulated as pharmaceuticals for non-pressurized preparations such as in a nebulizer or an atomizer.

The amount of the compounds of the present invention to be used varies according to the degree of the infection encountered, and the stages of the disease. A suitable dosage is about 0.5 to 100 mg/kg body weight. The preferred dosage is that amount sufficient to render a host asymptomatic to the particular viral infection. The dose may vary when the compounds are used prophylactically.

A method of treatment of retroviral infections utilizing the 2,3-epoxy compounds of the present invention can generally be by oral ingestion with a pharmaceutically acceptable carrier. The 2,3-epoxy compounds of the present invention can also be administered systemically, e.g., parenterally, via inhalation, or rectally to a person infected by retro virus.

Unit dosage forms for oral administration such as syrups, elixirs, and suspensions wherein each dosage unit, e.g., teaspoonful, tablespoonful, contains a predetermined amount of the 2,3-epoxy compound of the present invention. Inclusion of pharmaceutically acceptable excipients, are readily known by those skilled in the art. Parenteral administration of the 2,3-epoxy compounds of the present invention can be by a pharmaceutically acceptable carrier, such as Sterile Water for Injection, USP, or by normal saline.

The 2,3-epoxy compounds of the present invention can be administered rectally via a suppository. The suppository can include vehicles such as cocoa butter, carbowaxes and polyethylene glycols, which melt at body temperature, yet are solidified at room temperature.

The 2,3-epoxy compound of the present invention can be utilized in aerosol formulation to be administered via inhalation. The 2,3-epoxy compounds can be formulated into pressurized aerosol containers together with a pharmaceutically acceptable propellants such as dichlorodifluoromethane, propane, nitrogen and the like.

The term "unit dosage form" as used herein refers to physically discrete units suitable as unitary dosages for human and animal subjects, each unit containing a predetermined quantity of the 2,3-epoxy compound calculated in an amount sufficient to produce the desired to effect in association with a pharmaceutically acceptable, diluent, carrier or vehicle. The specifications for the novel unit dosage forms of the present invention depend on the particular compound employed and the effect to be achieved, and the pharmacodynamics associated with each compound in the host.

The pharmaceutically acceptable adjuvants, for example, vehicles, carrier of diluents are readily available to the public. The amount of the anti-retroviral 2,3-epoxy compound suitable for the various dosage forms can be determined by the particular anti-retroviral activity of each compound per se.

While not being bound to any theory, it is believed that the 2,3-epoxy compounds inhibit the essential protein enzyme necessary for viral replication. The details of the assay are set forth further in Copeland et al., Genetic Locus, Primary Structure, and Chemical Synthesis of Human Immunodeficiency Virus Protease, *Gene Anal Techn* 5:109–115 (1988).

Any necessary adjustments in dose can be readily made to meet the severity of the infection and adjusted accordingly by the skilled practitioner.

We claim:

1. An antiviral compound having the formula:

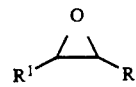

wherein R is $COR^5$; $R^5$ is a naturally occurring or synthetic amino acid bound via a terminal nitrogen on said naturally occurring or synthetic amino acid; and $R^1$ is aralkyl, aralkyl(lower alkyl)ether, $C_5$–$C_{13}$ alkyl(lower alkyl)ether, or $C_{5-13}$alkyl.

2. The compound according to claim 1, which is N-(2R-cis)-3-nonyloxiraneacyl-L-proline methyl ester.

3. An antiviral composition which comprises an antiviral effective amount of a compound according to claim 1, and a pharmaceutically acceptable carrier.

4. The antiviral composition according to claim 3, wherein said compound is N-(2R-cis)-3-nonyloxiraneacyl-L-proline methyl ester.

5. A method of treating HIV-I or HIV-II retroviral infections which comprises administering to a host in need thereof an effective antiviral amount of a compound according to claim 2.

6. The method according to claim 5, wherein said compound is N-(2R-cis)-3-nonyloxiraneacyl-L-proline methyl ester.

7. The method according to claim 5 wherein R and $R^1$ are trans to each other.

8. The method according to claim 5 wherein said retrovirus is HIV-I.

9. The method according to claim 5 wherein said retrovirus is HIV-II.